(12) United States Patent
Court et al.

(10) Patent No.: US 6,825,370 B2
(45) Date of Patent: Nov. 30, 2004

(54) CATALYST FOR ENANTIOSELECTIVE REDUCTION OF KETONES

(75) Inventors: Jean Court, Le Touvet (FR); Monique Lopez, Saint Paul de Varces (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 10/476,668
(22) PCT Filed: May 13, 2002
(86) PCT No.: PCT/FR02/01602
§ 371 (c)(1), (2), (4) Date: Nov. 4, 2003
(87) PCT Pub. No.: WO02/094837
PCT Pub. Date: Nov. 28, 2002

(65) Prior Publication Data
US 2004/0133021 A1 Jul. 8, 2004

(30) Foreign Application Priority Data
May 18, 2001 (FR) .......................... 01 06612

(51) Int. Cl.⁷ .................... C07F 15/00; B01J 21/02; C07C 27/00
(52) U.S. Cl. ................. 556/7; 502/202; 502/207; 568/814; 568/881
(58) Field of Search .................. 556/7; 502/202, 502/207; 568/814, 881

(56) References Cited

U.S. PATENT DOCUMENTS 6,218,585 B1 * 4/2001 Matos et al. ................ 568/814

OTHER PUBLICATIONS

Molvinger, K. et al:, :Asymmetric reduction of acetophenone over heterogeneous oxazaborolidine catalysts, Tetrahedron: Asymmetry (2000), 11 (11), 2263–2266.

Chemical Abstracts, vol. 132, No. 13, Mar. 27, 2000 (Mar. 27, 2000) Columbus, Ohio US;, abstract No. 167944, Molvinger, K. et al: "Asymmetric Reduction and Hydrogenation over Heterogeneous Catalysts Prepared by Reacting Nickel–Boride with Norephedrine", XP002189084, abrege & J. Mol. Catal. A: Chem. (1999), 150(1–2), 267–273.

Molvinger, Karine et al:, "Enantioselective borane reduction of ketones with oxazaborolidines boron–bound to nickel boride nanoparticles", Tetrahedron Lett. (1999), 40(48), 8375–8378.

* cited by examiner

Primary Examiner—Porfirio Nazario-Gonzalez
(74) Attorney, Agent, or Firm—Young & Thompson

(57) ABSTRACT

The invention concerns an oxazaborolidine compound fixed on a material selected among Raney nickel, Raney cobalt and Raney iron, the method for preparing same, and the use of the compound as reduction reaction catalyst of ketone to produce chiral alcohols.

17 Claims, 1 Drawing Sheet

CATALYST FOR ENANTIOSELECTIVE REDUCTION OF KETONES

Figure 1:
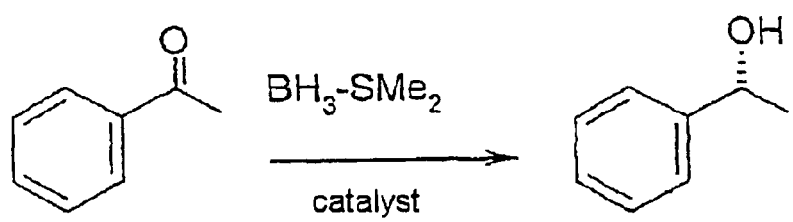
Figure 1:
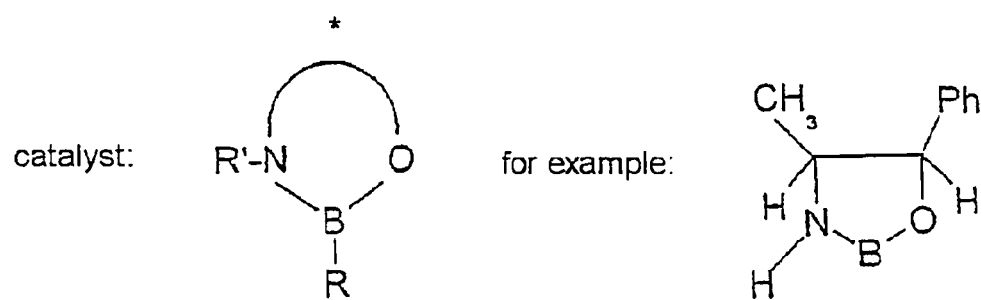

CROSS-REFERENCE TO RELATED APPLICATIONS.

This application is the National Stage Application under 35 U.S.C. 371 of International Application No. PCT/FR02/01602, filed May 13, 2002.

FIELD OF THE INVENTION

The present invention relates to a compound of oxazaborolidine type attached to a material chosen from Raney nickel, Raney cobalt and Raney iron, to its process of preparation and to the use of this compound as catalyst for the reaction of reduction of ketone to produce chiral alcohols.

BACKGROUND OF THE INVENTION

Chiral alcohols are often used in the pharmaceutical industry as intermediates in the synthesis of pharmaceutical active principles. Thus, the enantioselective reduction of prochiral ketones, which results in corresponding optically active secondary alcohols, is a subject of great interest.

Generally, the process comprises a reduction stage in which a prochiral ketone is reacted with a boron-based reducing agent in the presence of a catalyst of oxazaborolidine type. The boron-based reducing agent can be the dimethyl sulfide-borane complex or the tetrahydrofuran-borane complex or else the N,N-diethylaniline-borane complex or the 1,4-thioxane-borane complex. This reaction is represented in particular in FIG. 1. According to an alternative form of this process, the oxazaborolidine is replaced by its precursor, an aminoalcohol, which is converted in situ, during the reduction, to oxazaborolidine.

The attachment of these catalysts of oxazaborolidine type or precursors to insoluble polymers has already been described, this attachment allowing the catalyst to be easily separated from the reaction medium and optionally to be reused. Various chiral aminoalcohols have thus been bonded to crosslinked polystyrenes and then converted to polystyrene-oxazaborolidines (J. Chem. Soc. Perkin Trans., 1, 345–349 (1995); Tetrahedron: Asymmetry, Vol. 6, No. 11, pp. 2755–2766 (1995), Elsevier Science Ltd; J. Chem. Soc. Perkin. Trans., 1, 2887–2893 (1984)).

The process for attaching oxazaborolidine to polymers, such as polystyrenes, is complicated to employ since it generally consists in carrying out four stages. The final stage leads to the formation of water, which it is necessary to thoroughly remove. In addition, an organic polymer generally promotes the retention and the trapping of the molecules of reactants or products; consequently, it is often necessary to carry out several extractions or washings of said polymer. Furthermore, the catalytic reaction requires a stirring capable of denaturing the polymer used.

Compounds of oxazaborolidine type have also been attached to nickel nanoparticles (Tetrahedron Letters, 40 (1999), 8375–78). The process for the preparation of these compounds, which results in the formation of $NiB_2$, consists in reacting nickel iodide with lithium borohydride and then subsequently in mixing the suspension of $NiB_2$ in a solvent with norephedrine. However, the separation of these compounds used as catalyst in a reaction is not always easy.

BRIEF SUMMARY OF THE INVENTION

The aim of the present invention is thus to provide a novel type of catalyst which can be used in the preparation of chiral alcohols by reduction of prochiral ketones which exhibits satisfactory yields and satisfactory enantiomeric excesses.

Another aim of the present invention is to be able to make available a catalyst which readily separates from the solvent comprising the product obtained and thus to be able to reuse it without a significant decline in its performance.

These aims and others are achieved by the present invention, which relates to a compound of oxazaborolidine type attached to a material selected from Raney nickel, cobalt and iron.

Said materials are accessible to a person skilled in the art. They are generally found in the form of Raney grains with a diameter of 1000 to 10000 Å which correspond to agglomerates of crystallites with a diameter of 70 to 80 Å.

Preferably, the material is Raney nickel.

More specifically, this compound of oxazaborolidine type exhibits the following formula (I): $Ni_5B_{1-x}(oxaza)_x$, where x is a real number between 0 and 0.5 exclusive and oxaza exhibits the following formula:

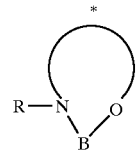

in which the nitrogen and oxygen atoms are connected, on the one hand, via a boron atom and, on the other hand, via a hydrocarbonaceous group, the star corresponds to the presence of at least one asymmetric carbon in said hydrocarbonaceous group, and R represents a hydrogen atom or an alkyl radical; optionally, the radical represented by R corresponds to a hydrocarbonaceous ring linked to the hydrocarbonaceous group connecting the nitrogen and oxygen atoms.

The most widely used hydrocarbonaceous radicals are alkyl, aryl or aralkyl radicals.

The term "alkyl radical" is understood to mean a saturated, linear, branched or cyclic, hydrocarbonaceous group comprising from 1 to 8 carbon atoms. Mention may in particular be made, as alkyl radicals, of the methyl, ethyl, 2-propyl, 1-butyl, neopentyl (2,2-dimethyl-1-propyl), 1-hexyl, cyclohexyl, cyclopentylmethyl or tert-octyl (1,1,3,3-tetramethyl-1-butyl) radicals.

The term "aryl" is understood in particular to mean the phenyl or β-naphthyl radical, optionally substituted by at least one substituent selected from an alkyl or alkyloxy radical and a halogen atom.

The term "aralkyl" is understood to mean, according to the invention, in particular Ω-arylalkyl, where the aryl radical and the alkyl radical are as defined above.

The hydrocarbonaceous group connecting the nitrogen and oxygen atoms is preferably a $C_2$ alkyl radical substituted by at least one alkyl or aryl radical.

Oxaza groups are described in particular in the above-mentioned publications. They are also disclosed in patents U.S. Pat. No. 4,943,635, U.S. Pat. No. 6,005,133, U.S. Pat. No. 6,037,505 and U.S. Pat. No. 6,025,531.

Preferably, the oxaza group is selected from the groups of following formulae:

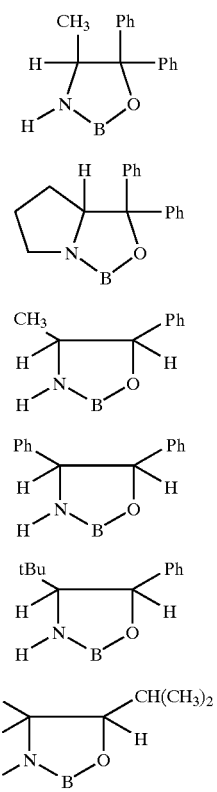

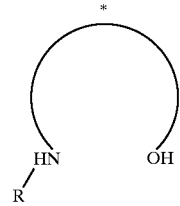

where Ph represents the phenyl radical and tBu represents the tert-butyl radical.

Advantageously, the oxaza group is selected from the groups of formulae (IV), (V), (VI) and (VII).

The compound of oxazaborolidine type according to the invention exhibits ferromagnetic characteristics which allow it to be easily separated from the reaction medium when it is used in particular as catalyst in a reaction for the reduction of prochiral ketone.

By way of comparison, the nickel nanoparticles which have reacted with boron do not exhibit ferromagnetic characteristics. Thus, no effect is observed on these particles when a magnetic field is applied.

The compound of oxazaborolidine type can also be separated from the reaction medium in which it is found by simple separation by settling.

The present invention additionally relates to a process for the preparation of the compound according to the invention which comprises the following stages:

(1) the material selected from Raney nickel, Raney cobalt and Raney iron is brought into contact with $BH_3$ in the presence of an inert solvent, (2) the product thus obtained is brought into contact with at least one aminoalcohol.

Preferably, the material used is Raney nickel.

The temperature of stages (1) and (2) according to the invention can vary to a large extent. It is generally between 0 and 60° C. Preferably, the temperature employed corresponds to ambient temperature (from 20 to 30° C.).

Stages (1) and (2) are preferably carried out under an inert atmosphere, such as, in particular, nitrogen or argon.

The inert solvent of the first reaction is selected more particularly from dioxane, diethyl ether, tetrahydrofuran, hexane, heptane, octane, cyclohexane, benzene, xylene and toluene. Preferably, tetrahydrofuran or diethyl ether is used.

Stage (2) is preferably carried out in a solvent, such as in particular one of those specified above.

More specifically, the aminoalcohol used has the general formula (VIII)

in which the hydrocarbonaceous group connecting the nitrogen and oxygen atoms and R are as defined above.

Preferably, these aminoalcohols are selected from β-aminoalcohols, such as α,α-diphenylpyrrolidine-methanol, (+)- or (−)-norephedrine, 2-amino-3-methyl-1-butanol (S or R), (1R,2S)- or (1S,2R)-2-amino-1,2-diphenylethanol, 2-amino-1,1-diphenyl-1-propanol (S or R) and 2-amino-3,3-dimethyl-1-butanol (S or R).

Preferably, before the reaction of $BH_3$ with the material, said material is reacted with a $BH_4^-$ ion, in particular in the form of lithium borohydride.

The amounts of the reactants can vary to a large extent.

Preferably, the amount of $BH_3$ used is such that the number of nickel, cobalt or iron atoms at the surface accessible to a reactant of the compound obtained is as low as possible. This amount varies according to the specific surface of the material used. To give an order of magnitude, the "$BH_3$ molecule/surface nickel, cobalt or iron atom" ratio advantageously varies between 0.5 and 5.

The present invention also relates to the use of the compound according to the invention as catalyst of a reaction for the reduction of prochiral ketone to produce chiral alcohols.

Thus, the reduction process comprises a treatment of a prochiral ketone, which has to be reduced to an optically active alcohol, with a boron-based reducing agent in the presence of a catalytically effective amount of a catalyst corresponding to the compound according to the present invention.

The term "catalytically effective amount" of a compound is understood to mean a substoichiometric amount which is sufficient to facilitate the conversion of a desired reactant to one or more products.

The term "enantiomeric excess (e.e.)" is understood to mean the excess of one of the two enantiomers over the other, generally expressed as a percentage. Thus, an enantiomeric excess of 90% corresponds to the presence of 95% of one enantiomer and of 5% of the other in the mixture in question.

The term "prochiral ketone", in particular represented by the formula $R_SR_LCO$, [lacuna] a compound exhibiting a ketone functional group in which $R_S$ and $R_L$ are not identical, so that the reduction product, a secondary alcohol, of formula $R_SR_LCHOH$ exhibits a chiral center on the carbon carrying the alcohol functional group.

Thus, a final subject matter of the present invention is a process for the enantioselective reduction of at least one prochiral ketone comprising a reaction of the prochiral ketone with a boron-based reducing agent in the presence of a compound according to the invention in a catalytically effective amount.

According to an alternative form of this process, the compound according to the invention is generated in situ.

The prochiral ketone having the formula $R_S R_L CO$ can be any prochiral ketone in which $R_S$ and $R_L$ are inert with respect to boron. $R_S$ and $R_L$ are, independently of one another, an organic radical, such as alkyl, aryl or aralkyl (the term "alkyl" is used here in its broadest sense, that is to say in the form of a nonaromatic hydrocarbonaceous radical, and consequently includes the alkenyl radical, and the term "aryl" means an aromatic hydrocarbonaceous radical and consequently includes the phenyl and naphthyl radical).

$R_S$ and $R_L$ can be taken together to form a ring with the carbon of the ketone functional group, such as, in particular, tetralone.

$R_S$ and $R_L$ can be independently substituted by any substituent which is inert with respect to boron, such as alkyl, alkoxy, halogen, and the like.

Of course, the enantioselective nature of the reduction process of the present invention depends to a certain extent on the relative sizes of $R_S$ and $R_L$.

The prochiral ketones more particularly used in the process according to the invention includes dialkyl ketones, such as t-butyl methyl ketone, 4-methyl-2-pentanone and methyl cyclohexyl ketone, alkyl aryl ketones, such as acetophenone, which is optionally substituted, para-methylacetophenone, para-fluoroacetophenone, propiophenone, chloroacetophenone and 2-acetyl-6-methoxynaphthalene, cyclic ketones, such as α-tetralone and 2-bromo-2-cyclohexen-1-one, and the like. Prochiral ketones which are already in the chiral form, for example prostaglandin intermediates, may also be suitable.

The alcohols which are produced according to the process of the invention can be used as chiral reactants, such as 1-phenylethanol, or as intermediate in a subsequent chemical synthesis, such as optically active 1-(6-methoxy-2-naphthyl)ethanol, a synthetic intermediate for naproxen.

The boron-based reducing agents are generally selected from dimethyl sulfide-borane, tetrahydrofuran-borane ($THF.BH_3$), N,N-diethylaniline-borane ($DENA.BH_3$) and 1,4-thioxane-borane complexes. $DENA.BH_3$ is preferred.

The reduction process according to the invention is carried out in an appropriate solvent, a solvent capable of diluting the ketone but which is inert to boron. Such solvents can in particular be nonbasic aprotic solvents, such as ethers (tetrahydrofuran, tetrahydropyran or diethyl ether) and aromatic hydrocarbons, such as benzene or toluene. The preferred solvents are ethers and more particularly tetrahydrofuran.

BRIEF DESCRIPTION OF THE DRAWING(S)

FIG. 1 depicts the reduction reaction of a prochiral ketone to produce a chiral alcohol in the presence of a catalyst of oxazaborolidine type.

DETAIL DESCRIPTION OF THE INVENTION

The examples which follow are presented by way of illustration and do not limit the present invention.

EXAMPLES 2 g of Raney nickel, washed beforehand with distilled water (50 ml×5) and with THF (50 ml×5), are suspended in 5 ml of THF under a nitrogen atmosphere; these conditions will be used for the various additions.

200 μl of a solution of $LiBH_4$ in THF (2M) are added; after 30 minutes, the catalyst is washed with THF (10 ml×2).

7.4 ml of $BH_3.THF$ solution (1M) are added over 1 hour to the anhydrous Raney nickel, the surface of which has been reduced; after 1 h at ambient temperature, the catalyst is washed with THF (10 ml×3); approximately 2 g of $Ni_5B$ (elemental analysis) are then available.

The aminoalcohol ($7.3 \times 10^{-4}$ mol) in 5 ml of THF is added; the THF rapidly turns cloudy; after one night at ambient temperature, the supernatant is removed and the catalyst is washed with THF (10 ml×4); approximately 2 g of $Ni_5B_{(1-0.125)}oxaza_{0.125}$ are then available.

Reduction Oxazaborolidine/ketone molar ratio=0.1; $BH_3$/ketone molar ratio=1 for the $BH_3.THF$ complex; $BH_3$/ketone molar ratio=1.3 for the $BH_3.DENA$ complex.

7.3 ml of 1M $BH_3.THF$ or 1.7 ml of DENA ($9.5 \times 10^{-3}$ mol) are added to $Ni_5B_{(1-0.125)}oxaza_{0.125}$ (approximately 2 g). After 20 minutes, $7.3 \times 10^{-3}$ mol of ketone in solution in THF (3 ml) are slowly added at 30° C. (1 h). After an additional 30 minutes, the catalyst is separated from the supernatant, which is stirred with 20 ml of methanol for 20 minutes, treated with 8 ml of HCl (1N) and extracted with ether. The ethereal solution is washed with a 1N HCl solution (only with DENA) and with a saturated NaCl solution. After drying and concentrating, the enantiomeric excess is determined by gas chromatography on a chiral capillary column and/or polarimetry.

The catalyst separated from the supernatant can be reused directly or after washing once with THF.

For the separation of the solid catalyst from the reaction mixture or from the wash liquor, halting the stirrer results in the catalyst becoming attached to the magnet and the liquid can be easily withdrawn, in particular with a syringe.

In the absence of a magnetic bar inside the round-bottomed flask, a magnet brought near the outside fulfills the same role. However, even without a magnet, separation by settling is very good and solid-liquid separation is easy and fast.

1) Catalyst resulting from the attachment of (1S,2R)-(+)-2-amino-1,2-diphenylethanol (Quallich).

a) Reduction of acetophenone (entries 1, 2, and 3); the complex with THF and the complex with diethylaniline (DENA) lead to similar results, markedly better results during the 2nd and 3rd use, to those obtained with dimethyl sulfide-borane.

b) Reduction of substituted acetophenones (entries 6 and 7); the $DENA.BH_3$ complex proves to be an excellent reducing agent.

c) Reduction of a cycloalkanone (α-tetralone) (entry 8); the enantioselective properties of the catalyst during its 1st use are very good.

d) Reduction of an aliphatic ketone (4-methy-2-pentanone) (entry 10); $DENA.BH_3$ has an undeniable effect.

2) Catalysts resulting from the addition of (+)-norephedrine and of (−)-norephedrine. These catalysts make possible the synthesis of each of the optical isomers of an alcohol. For example, (−)-norephedrine results predominantly in (R)-(+)-1-phenylethanol, (+)-norephedrine in (S)-(−)-1-phenylethanol. On reducing acetophenone with DENA (entry 5), the results are as good with norephedrine as with the alcohol from Quallich.

| Entry | Compound | Aminoalcohol | BH₃ Complex | Enantiomeric excess (%) | | |
|---|---|---|---|---|---|---|
| | | | | 1st use | 2nd | 3rd |
| 1 | Acetophenone | Quallich | THF.BH₃ | 90 | 85 | 75 |
| 2 | Acetophenone | Quallich | DENA.BH₃ | 89 | 86 | 77 |
| 3 | Acetophenone | Quallich | Dimethyl sulfide.BH₃ | 89 | 68 | 67 |
| 4 | Acetophenone | (−)-Norephedrine | THF.BH₃ | 85 | 75 | 63 |
| 5 | Acetophenone | (+)-Norephedrine | DENA.BH₃ | 90 | 83 | 77 |
| 6 | p-Methylacetophenone | Quallich | DENA.BH₃ | 94 | 86 | 85 |
| 7 | p-Fluoroacetophenone | Quallich | DENA.BH₃ | 98 | 91 | 90 |
| 8 | α-Tetralone | Quallich | DENA.BH₃ | 90 | 58 | 59 |
| 9 | α-Tetralone | (+)-Norephedrine | DENA.BH₃ | 81 | 85 | 70 |
| 10 | 4-Methyl-2-pentanone | Quallich | DENA.BH₃ | 87 | 62 | 54 |

Quallich: (1S,2R)-(+)-2-amino-1,2-diphenyethanol
DENA.BH₃: N,N-diethylaniline.BH₃
Norephedrine: C₆H₅CH(OH)CH(CH₃)NH₂

What is claimed is:

1. A compound of oxazaborolidine type attached to a material selected from Raney nickel, cobalt and iron.

2. The compound as claimed in claim 1, wherein the material is Raney nickel.

3. The compound as claimed in claim 2, wherein it exhibits the following formula (I): $Ni_5B_{1-x}(oxaza)_x$, where x is a real number between 0 and 0.5 exclusive and oxaza exhibits the following formula:

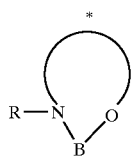

in which the nitrogen and oxygen atoms are connected, on the one hand, via a boron atom and, on the other hand, via a hydrocarbonaceous group, the star corresponds to the presence of at least one asymmetric carbon in said hydrocarbonaceous group, and R represents a hydrogen atom or an alkyl radical; optionally, the radical represented by R corresponds to a hydrocarbonaceous ring linked to the hydrocarbonaceous group connecting the nitrogen and oxygen atoms.

4. The compound as claimed in claim 3, wherein the hydrocarbonaceous group connecting the nitrogen and oxygen atoms is a $C_2$ alkyl radical substituted by at least one alkyl or aryl radical.

5. The compound as claimed in claim 4, wherein the oxaza group is selected from the groups of following formulae:

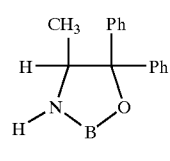
(II)

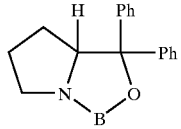
(III)

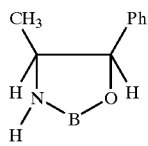
(IV)

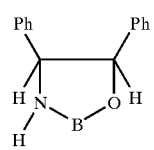
(V)

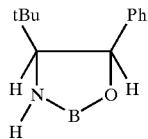
(VI)

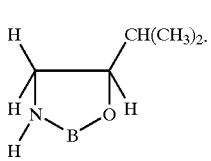
(VII)

6. The compound as claimed in claim 5, wherein the oxaza group is selected from the groups of formulae (IV), (V), (VI) and (VII).

7. A process for the preparation of the compound as claimed in claim 3 which comprises the following stages:

(1) the material selected from Raney nickel, Raney cobalt and Raney iron is brought into contact with BH₃ in the presence of an inert solvent, (2) the product thus obtained is brought into contact with at least one aminoalcohol.

8. The process as claimed in claim 7, wherein the material used is Raney nickel.

9. The process as claimed in claim 7, wherein the aminoalcohol used has the general formula:

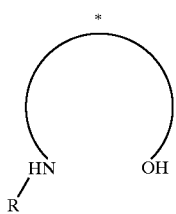

(VIII)

10. The process as claimed in claim 7, wherein the aminoalcohol is selected from α,α-diphenylpyrrolidinemethanol, (+)- or (−)-norephedrine, 2-amino-3-methyl-1-butanol (S or R), (1R,2S)- or (1S,2R)-2-amino-1,2-diphenylethanol, 2-amino-1,1-diphenyl-1-propanol (S or R) and 2-amino-3,3-dimethyl-1-butanol (S or R).

11. The process as claimed in claim 7, wherein the inert solvent is selected from dioxane, diethyl ether, tetrahydrofuran, hexane, heptane, octane, cyclohexane, benzene, xylene and toluene.

12. In the process for the reduction of prochiral ketone to produce chiral alcohols in the presence of a catalyst, wherein the improvement comprises the use of the compound as claimed in claim 1 as catalyst.

13. A process for the enantioselective reduction of at least one prochiral ketone comprising a reaction of the prochiral ketone with a boron-based reducing agent in the presence of a compound as claimed in claim 1 in a catalytically effective amount.

14. The reduction process as claimed in claim 13, wherein, according to an alternative form of this process, the compound as claimed in claim 1 is generated in situ.

15. The reduction process as claimed in claim 13, wherein the boron-based reducing agents are selected from dimethyl sulfide-borane, tetrahydrofuran-borane (THF.BH$_3$), N,N-diethylaniline-borane (DENA.BH$_3$) and 1,4-thioxane-borane complexes.

16. The reduction process as claimed in claim 15, wherein the reducing agent is DENA.BH$_3$.

17. A process for the preparation of the compound as claimed in claim 1 which comprises the following stages:
   (1) the material selected from Raney nickel, Raney cobalt and Raney iron is brought into contact with BH$_3$ in the presence of an inert solvent,
   (2) the product thus obtained is brought into contact with at least one aminoalcohol.

* * * * *